(12) United States Patent
Rao et al.

(10) Patent No.: US 6,376,727 B1
(45) Date of Patent: *Apr. 23, 2002

(54) PROCESSES FOR THE MANUFACTURE OF 1,1,1,3,3-PENTAFLUOROPROPENE, 2-CHLORO-PENTAFLUOROPROPENE AND COMPOSITIONS COMPRISING SATURATED DERIVATIVES THEREOF

(75) Inventors: V. N. Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,900

(22) PCT Filed: Feb. 18, 1998

(86) PCT No.: PCT/US98/03132

§ 371 Date: Aug. 19, 1999

§ 102(e) Date: Aug. 19, 1999

(87) PCT Pub. No.: WO98/37043

PCT Pub. Date: Aug. 27, 1998

(51) Int. Cl.[7] .................. C07C 17/00; C07C 17/25; B01D 3/34

(52) U.S. Cl. .............. 570/157; 570/165; 570/166; 570/168; 570/176; 203/67

(58) Field of Search .................. 570/157, 165, 570/166, 168, 176; 203/67

(56) References Cited

U.S. PATENT DOCUMENTS

| | | | |
|---|---|---|---|
| 2,942,036 A | 6/1960 | Smith et al. ............... 260/653 |
| 3,505,417 A | 4/1970 | Gardner ................... 260/653.5 |
| 3,636,173 A | 1/1972 | Gardner ................... 260/653.5 |
| 4,158,023 A | 6/1979 | Von Halasz |
| 5,057,634 A | 10/1991 | Webster et al. ............. 570/157 |
| 5,084,190 A | 1/1992 | Fernandez |
| 5,136,113 A | 8/1992 | Rao ......................... 570/176 |
| 5,169,873 A | 12/1992 | Behme et al. |
| 5,171,901 A | 12/1992 | Gassen et al. .............. 570/168 |
| 5,182,040 A | 1/1993 | Bartlett et al. |
| 5,196,616 A | 3/1993 | Lee et al. |
| 5,262,077 A | 11/1993 | Bivens et al. |
| 5,364,992 A | 11/1994 | Manogue et al. ........... 570/176 |
| 5,396,000 A | 3/1995 | Nappa et al. ............... 870/175 |
| 5,399,795 A | 3/1995 | Franz et al. ................ 570/165 |
| 5,444,102 A | 8/1995 | Nimitz et al. |
| 5,461,177 A | 10/1995 | Manzer et al. |
| 5,563,304 A | 10/1996 | Rao et al. .................. 570/166 |
| 5,626,725 A | 5/1997 | Balthasart et al. ............ 203/91 |
| 5,648,016 A | 7/1997 | Klug et al. |
| 5,725,791 A | 3/1998 | Bivens et al. |
| 5,856,587 A | 1/1999 | Visca et al. |
| 5,918,481 A | * 10/1999 | Pham et al. |
| 5,968,406 A | 10/1999 | Bartlett et al. |
| 6,107,267 A | 8/2000 | Rao et al. |
| 6,224,781 B1 | 5/2001 | Mahler et al. |

FOREIGN PATENT DOCUMENTS

| | | | |
|---|---|---|---|
| EP | 0 442 075 A1 | 8/1991 | ............ C07C/19/18 |
| EP | 0 634 384 A1 | 1/1995 | ......... C07C/17/087 |
| EP | 0 676 386 A1 | 10/1995 | ......... C07C/17/087 |
| WO | WO 90/08748 | 8/1990 | ............ C07C/17/00 |
| WO | WO 93/02150 | 2/1993 | ............ C09K/5/04 |
| WO | WO 95/04022 | 2/1995 | ............ C07C/17/23 |
| WO | WO 97/05089 | 2/1997 | ......... C07C/17/278 |
| WO | WO 97/19751 | 6/1997 | ............ B01J/23/58 |

OTHER PUBLICATIONS

09/713,128 Mahler et al.

* cited by examiner

*Primary Examiner*—Johann Richter
*Assistant Examiner*—Sikarl A. Witherspoon

(57) ABSTRACT

Disclosed are azeotropic compositions comprising $CF_3CHFCF_3$ and HF. Also disclosed are compositions and a process for producing compositions comprising (c1) $CF_3CHFCF_3$, $CF_3CH_2CF_3$, or $CHF_2CH_2CF_3$, and (c2) at least one saturated halogenated hydrocarbon and or ether having the formula: $C_nH_{2n+2-a-b}Cl_aF_bO_c$ wherein n is an integer from 1–4, a is an integer from 0–2n+1, b is an integer from 1–2n+2a, and c is 0 or 1, provided that when c is 1 then n is an integer from 2–4, and provided that component (c2) does not include the selected component (c1) compound, wherein the molar ratio of component (c2) to component (c1) is between about 1:99 and a molar ratio of HF to component (c1) in an azeotrope or azeotrope-like composition of component (c1) with HF. The process involves (A) combining (1) the azeotropic composition with (ii) the fluorination precursor to component (c2); and (B) reacting a sufficient amount of the HF from the azeotrope or azeotrope-like composition (1) with the precursor component (ii) to provide a composition containing components (c1) and (c2) in the desired ratio. The compositions include at least two (c1) compounds, at least one of which is an ether.

8 Claims, No Drawings

PROCESSES FOR THE MANUFACTURE OF 1,1,1,3,3-PENTAFLUOROPROPENE, 2-CHLORO-PENTAFLUOROPROPENE AND COMPOSITIONS COMPRISING SATURATED DERIVATIVES THEREOF

FIELD OF THE INVENTION

This invention relates to fluorine-substituted hydrocarbons, and more particularly to processes for producing $CF_3CH=CF_2$, $CF_3CCl=CF_2$ and saturated derivatives thereof such as $CF_3CH_2CF_3$, $CF_3CH_2CHF_2$ and $CF_3CHFCF_3$, and to compositions comprising the saturated derivatives (e.g., azeotropes of said saturated derivatives with HF and uses of said azeotropes).

BACKGROUND

A number of chlorine-containing halocarbons are considered to be detrimental toward the Earth's ozone layer. There is a world-wide effort to develop materials having lower ozone depletion potential that can serve as effective replacements. For example, the hydrofluorocarbon, 1,1,1,2-tetrafluoro-ethane (HFC-134a) is being used as a replacement for dichlorodifluoromethane (CFC-12) in refrigeration systems. The production of hydrofluorocarbons (i.e., compounds containing only carbon, hydrogen and fluorine), has been the subject of considerable interest to provide environmentally desirable products for use as solvents, blowing agents, refrigerants, cleaning agents, aerosol propellants, heat transfer media, dielectrics, fire extinguishants and power cycle working fluids (see, e.g., PCT International Publication No. WO 93/02150).

SUMMARY OF THE INVENTION

A process is provided in accordance with this invention for producing pentafluoropropenes of the formula $CF_3CX=CF_2$, where X is H or Cl. The process comprises hydrodehalogenating $CF_3CCl_2CF_3$ with hydrogen at an elevated temperature in the vapor phase over a catalyst comprising at least one component selected from the group consisting of elemental metals, metal oxides, metal halides and metal oxyhalides; wherein the metal of said hydrodehalogenation catalyst component is selected from copper, nickel, chromium and mixtures thereof and the halogen of said halides and said oxyhalides is selected from fluorine, chlorine and mixtures thereof.

This invention further provides a process for producing the hydrofluorocarbon $CF_3CHFCF_3$. This process comprises (a) hydrodehalogenating $CF_3CCl_2CF_3$ with hydrogen as indicated above to produce a product comprising $CF_3CCl=CF_2$, $CF_3CH=CF_2$, HCl and HF; and (b) reacting the $CF_3CCl=CF_2$ produced in (a) with HF to produce $CF_3CHFCF_3$.

This invention further provides a process for producing the hydrofluorocarbon $CF_3CH_2CHF_2$. This process comprises (a) hydrodehalogenating $CF_3CCl_2CF_3$ with hydrogen as indicated above to produce a product comprising $CF_3CCl=CF_2$, $CF_3CH=CF_2$, HCl and HF; and (b) reacting at least one of said $CF_3CCl=CF_2$ and $CF_3CH=CF_2$ produced in (a) in the vapor phase with hydrogen to produce $CF_3CH_2CHF_2$.

This invention further provides a process for producing $CF_3CH_2CF_3$. This process comprises (a) hydrodehalogenating $CF_3CCl_2CF_3$ with hydrogen as indicated above to produce a product comprising $CF_3CCl=CF_2$, $CF_3CH=CF_2$, HCl and HF; and (b) reacting the $CF_3CH=CF_2$ produced in (a) with HF to produce $CF_3CH_2CF_3$.

Azeotropic compositions (e.g., an azeotropic composition consisting essentially of from about 29.9 to about 41.3 mole percent HF and from about 70.1 to 58.7 mole percent $CF_3CHFCF_3$) are also provided which comprise $CF_3CHFCF_3$ and HF wherein said HF is present in an amount effective to form an azeotropic combination with said $CF_3CHFCF_3$.

The present invention further provides a process for recovering HF from a product mixture comprising HF and $CF_3CHFCF_3$. The process comprises (1) distilling the product mixture to remove all products which have a lower boiling point than the lowest boiling azeotrope containing HF and $CF_3CHFCF_3$; and (2) distilling said azeotrope to recover HF as an azeotropic composition containing HF and $CF_3CHFCF_3$.

This invention further provides a process for producing compositions comprising (c1) a compound selected from the group consisting of $CF_3CHFCF_3$, $CF_3CH_2CF_3$ and $CHF_2CH_2CF_3$ and (c2) at least one saturated compound selected from halogenated hydrocarbons and ethers having the formula:

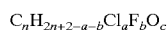

wherein n is an integer from 1 to 4, a is an integer from 0 to 2n+1 b is an integer from 1 to 2n+2−a, and c is 0 or 1, provided that when c is 1 then n is an integer from 2 to 4, and provided that component (c2) does not include the selected component (c1) compound, wherein the molar ratio of component (c2) to component (c1) is between about 1:99 and a molar ratio of HF to component (c1) in an azeotrope or azeotrope-like composition of component (c1) with HF. This process comprises (A) combining (i) said azeotrope or azeotrope-like composition with (ii) at least one fluorination precursor compound, wherein the precursor component (ii) is the fluorination precursor to component (c2); and (B) reacting a sufficient amount of the HF from the azeotrope or azeotrope-like composition (i) with precursor component (ii) to provide a composition containing components (c1) and (c2) in said ratio.

In addition, compositions are provided comprising: (c1) a compound selected from the group consisting of $CF_3CHFCF_3$, $CF_3CH_2CF_3$ and $CHF_2CH_2CF_3$; and (c2) at least two saturated compounds selected from halogenated hydrocarbons and ethers having the formula:

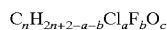

wherein n is an integer from 1 to 4, a is an integer from 0 to 2n+1, b is an integer from 1 to 2n+2−a, and c is 0 or 1, provided that when c is 1 then n is an integer from 2 to 4, provided that component (c2) does not include the selected component (c1) compound and provided that c is 1 for at least one of the component (c2) compounds, wherein the molar ratio of component (c2) to component (c1) is between 1:99 and 41.3:58.7 when component (c1) is $CF_3CHFCF_3$, between 1:99 and 59:41 when component (c1) is $CF_3CH_2CF_3$, and between 1:99 and 84:16 when component (c1) is $CHF_2CH_2CF_3$.

DETAILED DESCRIPTION

This invention provides a process for producing 1,1,1,3 3-pentafluoro-propane (i.e., $CF_3CH_2CHF_2$ or HFC-245fa) using 2,2-dichloro-1,1,1,3,3,3-hexafluoropropane (i.e., $CF_3CCl_2CF_3$ or CFC-216aa).

The present invention includes the hydrodehalogenation of CFC-216aa in a manner which removes a single fluorine from an end carbon while removing at least one chlorine from the internal carbon to produce $CF_3CCl=CF_2$ (CFC-1215xc) and $CF_3CH=CF_2$ (HCFC-1225zc). This hydrodehalogenation generally produces a product comprising $CF_3CCl=CF_2$, $CF_3CH=CF_2$, HF and HCl, and involves the use of advantageously catalytic components employing copper, nickel and/or chromium. Suitable components include halides such as CuF, CuCl, $CuCl_2$, CuClF, $NiF_2$, $NiCl_2$, NiClF, $CrF_3$, $CrCl_3$, $CrCl_2F$ and $CrClF_2$; oxides such as CuO, NiO, and $Cr_2O_3$; and oxyhalides such as copper oxyfluoride and chromium oxyfluoride. Oxyhalides may be produced by conventional procedures such as, for example, halogenation of metal oxides.

The catalysts of this invention may contain other components, some of which are considered to improve the activity and/or longevity of the catalyst composition. Preferred catalysts include catalysts which are promoted with compounds of molybdenum, vanadium, tungsten, silver, iron, potassium, cesium, rubidium, barium or combinations thereof. Also of note are chromium-containing catalysts which further contain zinc and/or aluminum or which comprise copper chromite.

The catalyst may be supported or unsupported. Supports such as metal fluorides, alumina and titania may be advantageously used. Particularly preferred are supports of fluorides of metals of Group IIB, especially calcium. A preferred catalyst consists essentially of copper, nickel and chromium oxides (each of said oxides being preferably present in equimolar quantities) preferably promoted with potassium salt, on calcium fluoride.

An especially preferred catalyst contains proportionally about 1.0 mole CuO, about 0.2 to 1.0 mole NiO, about 1 to 1.2 moles $Cr_2O_3$ on about 1.3 to 2.7 moles $CaF_2$, promoted with about 1 to 20 weight %, based on the total catalyst weight, of an alkali metal selected from K, Cs, and Rb (preferably K). When K is the promoter, the preferred amount is from about 2 to 15 weight % of the total catalyst.

This catalyst can be prepared by coprecipitating, from an aqueous medium, salts of copper, nickel and chromium (and optionally aluminum and zinc), with and preferably on calcium fluoride; washing, heating and drying the precipitate. An alkali metal compound (e.g., KOH, KF or $K_2CO_3$) is then deposited on the dried precipitate, followed by calcination to convert the copper, nickel and chromium to the respective oxides. Any soluble copper, nickel and chromium compound may be used, but the chlorides and nitrates are preferred, with the nitrates being especially preferred. Alternatively, promoters such as KOH, KF and $K_2CO_3$ may be added prior to co-precipitation.

Another group of catalysts which may be used for the conversion of $CF_3CCl_2CF_3$ contains proportionally about 1.0 mole CuO, about 0.2 to 1.0 mole NiO, about 1 to 1.2 moles $Cr_2O_3$, about 0.4 to 1.0 mole $MoO_3$, and about 0.8 to 4.0 mole $CaF_2$, optionally promoted with at least one compound from the group consisting of $MgF_2$, $MnF_2$, and $BaF_2$. Palladium or $WO_3$ may also be present.

The catalyst may be granulated, pressed into pellets, or shaped into other desirable forms. The catalyst may contain additives such as binders and lubricants to help insure the physical integrity of the catalyst during granulating or scraping the catalyst into the desired form. Suitable additives include carbon and graphite. When binders and/or lubricants are added to the catalyst, they normally, comprise about 0.1 to 5 weight percent of the weight of the catalyst.

The catalyst may be activated prior to use by treatment with hydrogen, air, or oxygen at elevated temperatures. After use for a period of time in the process of this invention, the activity of the catalyst may decrease. When this occurs, the catalyst may be reactivated by treating it with hydrogen, air or oxygen, at elevated temperature in the absence of organic materials.

The molar ratio of hydrogen to $CF_3CCl_2CF_3$ fed to the process typically ranges from about 1:1 to about 30:1, and is preferably at least about 3:1.

The hydrodehalogenation process of $CF_3CCl_2CF_3$ is suitably conducted at a temperature in the range of from about 300° C. to 450° C., preferably from about 350° C. to about 400° C. The contact time of reactants with the catalyst bed (i.e., the volume of the catalyst bed divided by the volumetric flow rate at the temperature and pressure of the reaction) is typically from about 5 seconds to about 4 minutes:

The product from the hydrodehalogenation reaction of $CF_3CCl_2CF_3$ comprises $CF_3CH=CF_2$, $CF_3CCl=CF_2$, HCl and HF and typically other compounds such as unreacted $CF_3CCl_2CF_3$ and partially reacted compounds such as $CF_3CHClCF_3$. These products may be separated by conventional means such as distillation and/or decantation and the components may be used individually. For example, $CF_3CH=CF_2$ (HFC-1225zc) may be used as a co-monomer for producing fluorine-containing polymers. Unreacted starting material (CFC-216aa) can be recycled to the hydrodehalogenation reactor.

Products from the hydrodehalogenation reaction of $CF_3CCl_2CF_3$ which contain the unreacted CFC-216aa and optionally also contain the partially reacted compound $CF_3CHClCF_3$, after isolation from the unsaturated hydrodehalogenation products, can also be further reacted with hydrogen (e.g., using a conventional supported palladium hydrogenation catalyst). This hydrogenation can be used to produce $CF_3CH_2CF_3$ (HFC-236fa), a useful fire extinguishant. If desired, the amount of HFC-236fa produced in this manner can be increased by decreasing the contact time of the CFC-216aa reactant in the hydrodehalogenation reactor.

$CF_3CCl=CF_2$ (CFC-1215xc) may be reacted with HF to produce $CF_3CHFCF_3$ (HFC-227ea), which is a useful fire extinguishant. The reaction is typically conducted at an elevated temperature in either the liquid or vapor phase using a fluorination catalyst. For example, $CF_3CCl=CF_2$ may be reacted with HF in the liquid phase at a temperature of from about 100 to 175° C. over a pentavalent antimony catalyst (e.g., $SbF_5$) to produce $CF_3CHFCF_3$; or $CF_3CCl=CF_2$ may be reacted with HF in the vapor phase at a temperature of from about 300 to 400° C. over an unsupported or supported trivalent chromium catalyst (e.g., $Cr_2O_3$ or $Cr_2O_3/AlF_3$). Of note are embodiments where the HF produced from the hydrodehalogenation of $CF_3CCl_2CF_3$ is used for $CF_3CHFCF_3$ production. Preferably, however, the mole ratio of HF to $CF_3CCl=CF_2$ used for $CF_3CHFCF_3$ production is at least about 5:1.

The reaction products from the hydrofluorination may be separated by conventional techniques, such as distillation. $CF_3CHFCF_3$ may form azeotropic combinations with HF and/or HCl; and conventional decantation/distillation may be employed if further purification of $CF_3CHFCF_3$ is desired.

An azeotrope is a liquid mixture that exhibits a maximum or minimum boiling point relative to the boiling points of surrounding mixture compositions. A characteristic of minimum boiling azeotropes is that the bulk liquid composition is the same as the vapor compositions in equilibrium therewith, and distillation is ineffective as a separation technique. It has been found, for example, that $CF_3CHFCF_3$ (HFC-227ea) and HF form a minimum boiling azeotrope. This azeotrope can be produced as a co-product with HFC-227ea. As discussed further below, compositions may be formed which consist essentially of azeotropic combinations of hydrogen fluoride with HFC-227ea. These include a composition consisting essentially of from about 29.9 to 41.3 mole percent HF and from about 70.1 to 58.7 mole percent HFC-227ea (which forms an azeotrope boiling at a temperature between about −25° C. and about 100° C. at a pressure between about 77 kPa and about 3764 kPa). The hydrofluorocarbons (e.g., HFC-227ea) can be separated from the HF in such azeotropes by conventional means such as neutralization and decantation. However, azeotropic compositions of hydrofluorocarbons and HF (e.g., an azeotrope recovered by distillation of fluorination reactor effluent) are useful as recycle to the fluorination reactor, where the recycled HF can function as a reactant and the recycled hydroluorocarbon can function to moderate the temperature effect of the heat of reaction. Thus, for example, the process of this invention for producing $CF_3CHFCF_3$ can further comprise the steps of recovering a portion of the $CF_3CHFCF_3$ as an azeotropic composition of $CF_3CHFCF_3$ and HF and recycling said azeotropic composition to the reactor.

$CF_3CH=CF_2$ (CFC-1225zc) may be reacted with HF to produce $CF_3CH_2CF_3$ (HFC-236fa), which is a useful fire extinguishant. The reaction is typically done in either the liquid or vapor phase with or without using a fluorinating catalyst. For example, $CF_3CH=CF_2$ may be reacted with HF in the liquid phase at a temperature of from about 20° C. to about 175° C. in the absence of a catalyst to produce $CF_3CH_2CF_3$; or $CF_3CH=CF_2$ may be reacted with HF in the liquid phase at a temperature of from about 0° C. to about 175° C. over a polyvalent metal halide catalyst (e.g., $SbF_5$, $AlF_3$, $MoF_5$, $TaF_5$, $NbF_5$, $SnCl_4$, $SbCl_5$ or $TiCl_4$) to produce $CF_3CH_2CF_3$. Also, $CF_3CH=CF_2$ may be reacted with HF in the vapor phase at a temperature of from about 150° C. to about 400° C. in the absence of a catalyst to produce $CF_3CH_2CF_3$; or $CF_3CH=CF_2$ may be reacted with HF in the vapor phase at a temperature of from about 50° C. to about 400° C. over an unsupported or supported trivalent chromium catalyst (e.g., $Cr_2O_3$ or $Cr_2O_3/AlF_3$) or other vapor phase fluorination catalysts such as $AlF_3$, carbon or a transition metal (e.g., Co, Mn, and/or Cr) supported on $AlF_3$. Of note are embodiments where the HF produced from the hydrodehalogenation of $CF_3CCl_2CF_3$ is used for $CF_3CH_2CF_3$ production. Preferably, however, the mole ratio of HF to $CF_3CH=CF_2$ used for $CF_3CH_2CF_3$ production is at least about 1:1. Reference is made to U.S. Pat. No. 5,563,304 for a discussion of vapor phase hydrofluorination.

The reaction products from the hydrofluorination may be separated by conventional techniques, such as distillation. $CF_3CH_2CF_3$ forms an azeotrope with HF (see U.S. Pat. No. 5,563,304) and may also form all azeotrope with HCl; and conventional decantation/distillation may be employed if further purification of $CF_3CH_2CF_3$ is desired. The azeotropic compositions of $CF_3CH_2CF_3$ include a composition consisting essentially of from about 59 to 37 mole percent HF and from about 41 to 63 mole percent $CF_3CH_2CF_3$ (which forms an azetrope having a boiling point from about −25° C. at 44 kPa to about 100° C. at 2900 kPa).

In another embodiment, the HFC-1225zc and/or CFC-1215xc produced by the hydrodehalogenation reaction of this invention may be reacted with hydrogen in the vapor phase to produce $CF_3CH_2CHF_2$. The reaction of $CF_3CCl=CF_2$ and/or $CF_3CH=CF_2$ with hydrogen can employ a hydrogenation catalyst. Suitable hydrogenation catalysts include those which contain a metal (e.g., a Group VIII metal or rhenium). The metal may be supported (e.g., Pd supported on alumina, aluminum fluoride, or carbon) or may be unsupported (e.g., Raney nickel). Carbon-supported metal catalysts are preferred, with Pd/C being particularly preferred. The carbon support is preferably washed with acid prior to depositing the metal on it. Procedures for preparing a catalyst of Group VIII metal or rhenium on an acid-washed carbon support are disclosed in U.S. Pat. No. 5,136,113, the entire contents of which are hereby, incorporated by reference.

Of note is a process where $CF_3CCl=CF_2$ and/or $CF_3Cl=CF_2$ is contacted with hydrogen in the presence of a hydrogenation catalyst and in the presence of HCl and HF. The $CF_3CH=CF_2$ and/or $CF_3CCl=CF_2$ may be isolated from the hydrodehalogenation reaction effluent by distillation if desired, and then passed to the hydrogenation step, with HCl and HF beings separately added in the hydrogenation step. However, it is preferred to pass the HCl and HF from the hydrodehalogenation, and more preferably the entire effluent from the hydrodehalogenation of $CF_3CCl_2CF_3$ (including the $CF_3CCl=CF_2$, $CF_3CH=CF_2$, HCl and HF), with hydrogen over the hydrogenation catalyst. While the hydrogenation reaction proceeds even in the absence of HCl and HF, the HCl and HF present during the hydrogenation step moderates the hydrogenation reaction. In any case, in accordance with this invention, $CF_3CH_2CHF_2$ may be produced from $CF_3CCl_2CF_3$ without separation and removal of HCl and HF prior to $CF_3CH_2CHF_2$ production. In addition, passing the entire effluent from the hydrodehalogenation step on to the hydrogenation step avoids handling concerns associated with olefinic halogenated compounds as well as HCl and HF. The HCl and HF of the hydrogenation effluent is available for use along with other compounds thereof. For example, the HF is available for azeotropic combination with the fluorinated hydrocarbon compounds of the effluent from the hydrogenation reaction.

The contact of said hydrodehalogenation effluent with hydrogen in the presence of a hydrogenation catalyst and HCl and HF is suitably conducted at a temperature in the range of from about 50° C. to about 300° C., and preferably from about 50° C. to about 200° C. Contact time is typically from about 5 to 100 seconds, preferably about 10 to 30 seconds.

The molar ratio of hydrogen to $CF_3CH=CF_2$ in the hydrodehalogenation effluent typically is in the range from about 1:1 to about 50:1, and is preferably from about 1.5:1 to about 25:1, and more preferably from about 2:1 to about 10:1. Normally, at least about 100 ppm each of HCl and HF is present; and typically for each mole of $CF_3CH=CF_2$, the hydrodehalogenation effluent also contains two moles of HCl and one mole of HF, especially when the entire effluent from the hydrodehalogenation step is passed to the hydrogenation step.

Hydrogen can be fed to the hydrodehalogenation and/or the hydrogenation steps either in the pure state or diluted with inert gas (e.g., nitrogren, helium or argon).

Alternatively, $CF_3CH_2CHF_2$ may be produced by reacting the $CF_3CH=CF_2$ and/or $CF_3CCl=CF_2$ hydrodehalogenation reaction product with hydrogen in an empty reaction vessel of nickel, iron or their alloys in accordance with the disclosure of U.S. Pat. No. 5,364,992, which is incorporated herein in its entirety by reference.

The reaction products from the hydrogenation may be separated by conventional techniques, such as distillation. $CF_3CH_2CHF_2$ forms an azeotrope with HF (see PCT International Publication No. WO97/05089) and may also form an azeotrope with HCl; and conventional decantation/distillation may be employed if further purification of $CF_3CH_2CHF_2$ is desired. The azeotropic compositions of $CF_3CH_2CHF_2$ include a composition consisting essentially of from about 84 to 44 mole percent HF and from about 16 to 56 mole percent $CF_3CH_2CHF_2$ (which forms an azeotrope having a boiling point from about −50° C. at 5.5 kPa to about 130° C. at 3853 kPa).

Pressure is not critical for the hydrofluorination, hydrogenation, and hydrodehalogenation processes described above. Atmospheric and superatmospheric pressures (e.g., pressure from about 100 kPa to 7000 kPa) are the most convenient and are therefore preferred.

The hydrofluorination, hydrogenation and hydrodehalogenation reactions may be conducted in any suitable reactor.

The reaction vessel should be constructed from materials which are resistant to the corrosive effects of hydrogen fluoride such as Inconel™ nickel alloy and Hastelloy™ nickel alloy.

The $CF_3CCl_2CF_3$ used as a reactant in this process may be produced by known art methods such as disclosed in U.S. Pat. No. 5,057,634.

$CF_3CH_2CHF_2$ has numerous uses including applications in compositions used as refrigerants, blowing agents, propellants, cleaning agents, and heat transfer agents.

HFC-227ea/HF Azeotrope

As noted above, the present invention provides a composition which consists essentially of hydrogen fluoride and an effective amount of $CF_3CHFCF_3$ to form an azeotropic composition with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the components, and which will provide a vapor composition essentially identical to the liquid composition undergoing boiling.

For the purpose of this discussion, azeotrope-like compositions means a composition that behaves like an azeotrope (i.e., has constant-boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432–439). Experimental identification of azeotropic compositions involving the same components may be used to confirm the accuracy of such calculations and/or to modify the calculations at the same or other temperatures and pressures.

It has been found that azeotropes of HFC-227ea and HF are formed at a variety of temperatures and pressures. Between 78 kPa (at a temperature of −25° C.) and 3764 kPa (at a temperature of 100° C.) azeotropic compositions consisting essentially of HFC-227ea and HF range from about 29.9 mole percent HF (and 70.1 mole percent HFC-227ea) to about 41.3 mole percent HF (and 58.7 mole percent HFC-227ea). An azeotrope of HF and $CF_3CHFCF_3$ has been found at −10° C. and 21.9 psia (151 kPa) consisting essentially of about 40.9 mole percent HF and about 59.1 mole percent HFC-227ea). An azeotrope of HF and $CF_3CHFCF_3$ has also been found at 70° C. and 261.2 psia (1800 kPa) consisting essentially of about 37.0 mole percent HF and about 63.0 mole percent HFC-227ea. Based upon the above findings, it has been calculated that an azeotropic composition of about 41.3 mole percent HF and 58.7 mole percent HFC-227ea can be formed at −25° C. and 78 kPa and an azeotropic composition of about 29.9 mole percent HF and 70.1 mole percent HFC-227ea can be formed at 125° C. and 3764 kPa. Accordingly, the present invention provides an azeotrope or azeotrope-like composition consisting essentially of from about 29.9 to about 41.3 mole percent HF and from about 70.1 to 58.7 mole percent HFC-227ea, said composition having a boiling point from about −25° C. to 78 kPa to about 100° C. at 3764 kPa.

Processes may employ azeotropic distillation of HF with a compound selected from the group consisting of $CF_3CHFCF_3$, $CF_3CH_2CF_3$ and $CHF_2CH_2CF_2$. Product mixtures obtained from a variety of sources can be distilled. These sources include product mixtures produced by fluorination with HF of $CF_3CF=CF_2$ to afford HFC-227ea/HF, fluorination with HF of $CCl_3CH_2CCl_3$ to afford HFC-236fa/HF and fluorination with HF of $CHCl_2CH_2CCl_3$ to afford HFC-245fa/HF. The described catalytic fluorination with HF reactions can be done in either the liquid or vapor phase using procedures known in the art. The product mixture may be distilled to remove all products which have a lower boiling point than the lowest boiling azeotrope containing HF and a compound selected from the group consisting of HFC-227ea, HFC-236fa and HFC-245fa. Such low-boiling, materials can include, for example, HCl. For continuous processes, distillate and azeotropes with higher boiling points can be advantageously removed from appropriate sections of the distillation column. The lowest boiling azeotrope containing HF and one of the following compounds, $CF_3CHFCF_3$, $CF_3CH_2CF_3$ or $CHF_2CH_2CF_3$ may then be distilled such that HF is recovered as an azeotropic composition containing HF together with one of the following compounds, $CF_3CHFCF_3$, $CF_3CH_2CF_3$ or $CHF_2CH_2CF_3$.

Where the mixture (after distilling components boiling at lower temperatures than the lowest boiling azeotrope of HF with $CF_3CHFCF_3$) consists essentially of HF and $CF_3CHFCF_3$, HF may be recovered as an azeotrope consisting essentially of $CF_3CHFCF_3$ and HF. If excess amounts of $CF_3CHFCF_3$ or HF remain after azeotropes are recovered from these mixtures, such excess may be recovered as a relatively pure compound. The distillation of azeotropes containing HF and $CF_3CHFCF_3$ may be done at a wide variety of temperatures and pressures. Typically the temperature is between about −25° C. and about 125° C. and the pressure is between 78 kPa and 3764 kPa. The process of this invention includes embodiments where azeotropic compositions containing from about 58.7 to about 70.1 mole percent $CF_3CHFCF_3$ are recovered. HF may be recovered for example, from a product mixture including $CF_3CHFCF_3$ formed by the reaction of $CF_3CF=CF_2$ with HF.

Where the mixture (after distilling components boiling at lower temperatures than the lowest boiling azeotrope of HF with $CF_3CH_2CF_3$) consists essentially of HF and $CF_3CH_2CF_3$, HF may be recovered as an azeotrope consisting essentially of $CF_3CH_2CF_3$ and HF. If excess amounts of $CF_3CH_2CF_3$ or HF remain after azeotropes are recovered from these mixtures, such excess may be recovered as a relatively pure compound. The distillation of azeotropes containing HF and $CF_3CH_2CF_3$ may be done at a wide variety of temperatures and pressures. Typically the temperature is between about −25° C. and about 100° C. and the pressure is between 44 kPa and 2900 kPa. The process of this invention includes embodiments where azeotropic compositions containing from about 31 to about 63 mole percent $CF_3CH_2CF_3$ are recovered. HF may be recovered for example, from a product mixture including $CF_3CH_2CF_3$ formed by the reaction of $CCl_3CH_2CCl_3$ with HF.

Where the mixture (after distilling components boiling at lower temperatures than the lowest boiling azeotrope of HF with $CHF_2CH_2CF_3$) consists essentially of HF and $CHF_2CH_2CF_3$, HF may be recovered as an azeotrope consisting essentially of $CHF_2CH_2CF_3$ and HF. If excess amounts of $CHF_2CH_2CF_3$ or HF remain after azeotropes are recovered from these mixtures, such excess may be recovered as a relatively pure compound. The distillation of azeotropes containing HF and $CHF_2CH_2CF_3$ may be done at a wide variety of temperatures and pressures. Typically the temperature is between about −50° C. and about 130° C. and the pressure is between 5.5 kPa and 3850 kPa. The process of this invention includes embodiments where azeotropic compositions containing from about 16 to about 56 mole percent $CHF_2CH_2CF_3$ are recovered. HF may be recovered for example, from a product mixture including $CHF_2CH_2CF_3$ formed by the reaction of $CHCl_2CH_2CCl_3$ with HF.

The HFC-227ea/HF azeotrope, as well as the HFC-236fa/HF and HFC-245fa/HF azeotropes can be used as an HF source to fluorinate numerous compounds. Optionally, such fluorinations can employ a fluorination catalyst. The fluorinations can be done in the liquid phase using typical catalysts such as $SbCl_5$. The fluorinations can also be done in the vapor phase using typical catalysts such as $Cr_2O_3$. The following compounds, either individually or in mixed blends, can be fluorinated with the HF azeotrope to provide a variety of compositions wherein the ratio of the fluorination product(s) to a compound selected from the group consisting of $CF_3CHFCF_3$, $CF_3CH_2CF_3$ and $CHF_2CH_2CF_3$ is about 1:99, or more (depending upon the azeotropic combination of $CF_3CHFCF_3$, $CF_3CH_2CF_3$ or $CHF_2CH_2CF_3$ and HF used, and the degree of fluorination).

By fluorination precursors to the component (c2) compound(s) is meant compounds which react with HF (optionally in the presence of a fluorination catalyst) to produce the corresponding component (c2) compound(s). Fluorination precursors include saturated compounds having the formula

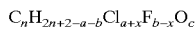

wherein x is an integer from 1 to b. Examples of saturated precursors and corresponding products are as follows:

| SATURATED PRECURSOR | PRODUCT |
|---|---|
| $CH_2Cl_2$ | $CH_2CF_2$ |
| $CHCl_2CHCl_2$ | $CHF_2CHF_2$ |
| $CF_3CH_2Cl$ | $CF_3CH_2F$ |
| $CH_2ClCF_2CHF_2$ | $CH_2FCF_2CHF_2$ |
| $CH_3CF_2CCl_3$ | $CH_3CF_2CF_3$ |
| $CHCl_2CH_2CCl_3$ | $CHF_2CH_2CF_3$ |
| $CHCl_2OCF_2CHF_2$ | $CHF_2OCF_2CHF_2$ |
| $CF_3CHClOCHF_2$ | $CF_3CHFOCHF_2$ |
| $CHF_2OCHCl_2$ | $CHF_2OCHF_2$ |
| $CClF_2OCHF_2$ | $CF_3OCHF_2$ |

Fluorination precursors also include unsaturated compounds having the formula

wherein y is an integer from 0 to b-1. Examples of unsaturated precursors and corresponding products are as follows:

| UNSATURATED PRECURSOR | PRODUCT |
|---|---|
| $CH_2=CF_2$ | $CH_3CF_3$ |
| $CH_2=CH_2$ | $CH_3CH_2F$ |
| $CH_2=CCl_2$ | $CH_3CCl_2F$ |
| $CF_3CH=CH_2$ | $CF_3CH_2CH_2F$ |
| $CF_2CCl=CCl_2$ | $CF_3CHClCClF_2$ |
| $CF_3CF=CHF$ | $CF_3CHFCHF_2$ |
| $CF_3CH=CF_2$ | $CF_3CH_2CF_3$ |
| $CF_3OCF=CF_2$ | $CF_3OCHFCF_3$ |

Of particular note are processes where for component (b) a is 0 and b is 2n+1, or less.

These fluorinations include processes for producing compositions wherein the molar ratio of component (c2) to $CF_3CHFCF_3$ is between about 1:99 and about 41.3:58.7; the molar ratio of component (c2) to $CF_3CH_2CF_3$ is between about 1:99 and about 59:41; and the molar ratio of component (c2) to $CHF_2CH_2CF_3$ is between about 1:99 and about m84:16. This process comprises (A) combining (i) an azeotrope or azeotrope-like composition consisting essentially of $CF_3CHFCF_3$, $CF_3CH_2CF_3$ of $CHF_2CH_2CF_3$ and HF wherein the ratio of HF, to the (c1) component is at least equal to the desired ratio of component (c2) to the respective component (c1) compound with the precursor component (ii).

Of note are embodiments of this fluorination where the $CF_3CHFCF_3$/HF, $CF_3CH_2CF_3$/HF or $CHF_2CH_2CF_3$/HF azeotropes combined with the precursor(s) is obtained by (1) distilling a product mixture comprising HF and a compound selected from the group consisting of $CF_3CHFCF_3$, $CF_3CH_2CF_3$ and $CHF_2CH_2CF_3$ to remove all products which have a lower boiling point than the lowest boiling azeotropic contains HF and said compound; and (2) distilling said azeotrope to recover HF as an azeotropic composition containing HF and said compound. Also of note are processes where the fluorination precursors include precursors for at least two saturated compounds of the formula $C_nH_{2n+2-a-b}Cl_aF_bO_c$, where c is 1 for at least one of said saturated compounds.

The fluorination product components containing component (c1) and component (c2) may be separated by conventional means such as distillation, selective sorption and/or decantation. The compositions of this invention comprising components (c1) and (c2) (including at least one ether) are useful, for example, as aerosol propellants, fire extinguishants, and/or refrigerants. Some of the compounds of the component (c2) combinations may form HCl azeotropes. The HCl can be separated from those combinations by extractive distillation or sorption on activated carbon. A number of the combinations may boil too close together to separate by distillation, forming azeotropic blends (i.e., blends boiling within a limited temperature range). Some of the combinations may form binary or even ternary azeotropes. The azeotropes, zeotropes and individual compounds can be collected from different parts of a distillation column.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

Hydrodehalogenation Catalyst Preparation for the Examples

Aqueous calcium nitrate (2.7 moles) is mixed with aqueous potassium fluoride (5.4 moles), heated and stirred briefly at 100° C. to form a slurry of $CaF_2$. To this slurry is added copper nitrate (1 mole), nickel nitrate (1 mole) and chromium nitrate (1 mole) as solids. The slurry is stirred at 70 to 80° C. until the salts, other than $CaF_2$, dissolve. This is followed by adding 0.1 mole of aqueous potassium hydroxide over 1 hour and boiling the mixture briefly. The slurry is cooled to 40 to 50° C. and filtered. The solid is washed exhaustively to reduce the potassium content to an undetectable level. After drying, potassium hydroxide is added as a solution in quantities sufficient to provide a catalyst containing 9 weight % potassium. After drying again, the catalyst is calcined at 600° C. for 8 to 16 hours, then granulated and screened to 1 to 2 mm particles. The catalyst is mixed with 1 to 5 wt % "Sterotex" powdered lubricant (registered trademark of Capital City Products Co., Columbus Ohio, division of Stokely-Van Camp, for its edible hydrogenated vegetable oil) to give 1/8"×1/8' (3.2 mm×3.2 mm) cylindrical pellets from a Stokes tablet machine.

General Procedure for Product Analysis for the Examples

The products leaving the reactor were analyzed on line using a gas chromatograph. The column consisted of a 20' (6.1 m)×1/8" (3.2 mm) stainless steel tube containing Krytox™ perfluorinated polyether on an inert support. Helium was used as the carrier gas. The product analyses are reported in mole %.

Legend

| | |
|---|---|
| 143a is $CF_3CH_3$ | 125 is $CF_3CHF_2$ |
| 216aa is $CF_3CCl_2CF_3$ | 226da is $CF_3CHClCF_3$ |
| 236fa is $CF_3CH_2CF_3$ | 235da is $CF_3CHClCHF_2$ |
| 225da is $CF_3CHClCClF_2$ | 245fa is $CF_3CH_2CHF_2$ |
| 254fb is $CF_3CH_2CH_2F$ | 1225zc is $CF_3CH=CF_2$ |
| 1215xc is $CF_3CCl=CF_2$ | CT is contact time |
| HFP is $CF_3CF=CF_2$ | conv. is conversion |
| | sel. is selectivity |

Example 1

A 15" (381 mm)×1/4" (6.4 mm) O. D. Inconel™ 600 nickel alloy U-tube reactor used for hydrodehalogenation (HDH) was charged with catalyst (21.7 g, 18 mL) pellets prepared substantially in accordance with the Catalyst Preparation described above. The HDH catalyst was in use for a variety of runs totaling 646 hours prior to its use in Example 1. Before starting the runs shown in Example 1, the HDH catalyst was regenerated with 50 sccm ($8.3×10^{-7}$ m$^3$/s) 50% air/50% $N_2$ at 350° C. for 1 hour; 50 sccm ($8.3×10^{-7}$ m$^3$/s) air at 400° C. for 2 hours; followed by purging with 200 sccm ($3.3×10^{-6}$ m$^3$/s) $N_2$ at 400° C. for 40 minutes; and finally reduced with 50 sccm ($8.3×10^{-7}$ m$^3$/s) $H_2$ at 300° C. for 75 minutes.

$CF_3CCl_2CF_3$ and $H_2$ were contacted with the catalyst at 350° C. or 360° C. and with a molar ratio of $H_2$:$CF_3CCl_2CF_3$ as shown in the table. Runs 1 to 3 were conducted at a pressure of 40 psig (380 kPa) and runs 4 to 9 were done at 100 psig (790 kPa). Results of the HDH reaction are shown in Table 1.

TABLE 1

| Run | HDH | Molar Ratio | CT | % Conv. | % Sel. to | | | | |
|---|---|---|---|---|---|---|---|---|---|
| No. | T (° C.) | $H_2$:216aa | Min. | 216aa | 1225zc | 236fa | 245fa | 1215xc | 226da |
| 1 | 350 | 7 | 0.58 | 92.9 | 12.5 | 0.1 | 0.2 | 75.9 | 6.4 |
| 2 | 350 | 12 | 0.58 | 99.3 | 15.7 | 0.3 | 0.2 | 72.9 | 5.4 |
| 3 | 360 | 12 | 0.57 | 99.5 | 19.1 | 0.5 | 0.3 | 71.6 | 3.4 |
| 4 | 360 | 10 | 0.54 | 99.3 | 23.0 | 0.6 | 0.4 | 67.4 | 3.7 |
| 5 | 360 | 22 | 0.55 | 99.4 | 21.4 | 0.6 | 0.4 | 72.6 | 1.2 |
| 6 | 350 | 22 | 0.56 | 99.4 | 14.6 | 0.4 | 0.2 | 78.4 | 2.8 |
| 7 | 350 | 11 | 0.56 | 99.0 | 11.1 | 0.3 | 0.1 | 78.8 | 6.5 |
| 8 | 360 | 11 | 0.55 | 99.2 | 12.5 | 0.3 | 0.2 | 77.1 | 6.6 |
| 9 | 360 | 22 | 0.55 | 99.4 | 17.3 | 0.5 | 0.2 | 76.8 | 1.9 |

[1]HDH is the hydrodehalogenation catalyst

Example 2

A second reactor for hydrogenation was added to the system on the exit side of the HDH reactor. This reactor consisted of an Inconel™ 600 tube 3/8" (9.5 mm) od.×0.035" (0.9 mm) wall, 30" (762 mm) long packed with 21.8 grams (18.0 mL) of (0.5 weight % palladium on acid washed 12–30 mesh carbon (1.68–0.59 mm). The catalyst was treated with 50 sccm ($8.3×10^{-7}$ m$^3$/s) of hydrogen at 100° C. for 15 hours prior to the run. The HDH reactor was the same as that used in Example 1. It was packed with 21.7 g of the HDH catalyst and treated with 50 sccm ($8.3×10^{-7}$ m$^3$/s) at 350° C. for 15 hours prior to the run. The entire effluent of the HDH reactor (including HCl and HF) was passed into the second (hydrogenation) reactor. The contact time in the HDH reactor was 0.27 minutes except for runs 4 and 5 where it was 0.29 minutes. The temperature for the HDH reaction was 350° C. for all the runs. The contact time (CT) shown in the table is for the Pd/C catalyst. The pressure of both reactors was 40 psig (377 kPa). Results of these reactions are shown in the Table 2.

TABLE 2

| Run | Pd/C | Molar Ratio | CT | % Conv. | % Sel. to | | | | |
|---|---|---|---|---|---|---|---|---|---|
| No. | T (° C.) | $H_2$:216aa | Min. | 216aa | 1225zc | 245fa | 254fb | 226da | 235da | 225da |
| 1 | 100 | 16 | 0.45 | 99.5 | 24.3 | 57.5 | <0.1 | 2.9 | 12.1 | 0.7 |
| 2 | 100 | 8 | 0.45 | 99.4 | 40.3 | 40.0 | 0.6 | 4.3 | 10.7 | 1.0 |
| 3 | 80 | 8 | 0.48 | 99.1 | 40.9 | 25.4 | 0.5 | 5.1 | 13.7 | 1.4 |

TABLE 2-continued

| Run No. | Pd/C T (° C.) | Molar Ratio H$_2$:216aa | CT Min. | % Conv. 216aa | % Sel. to | | | | | |
|---|---|---|---|---|---|---|---|---|---|---|
| | | | | | 1225zc | 245fa | 254fb | 226da | 235da | 225da |
| 4  | 80  | 15 | 0.50 | 99.2 | 42.7 | 22.7 | 0.4 | 4.3 | 15.2 | 1.2 |
| 5  | 150 | 15 | 0.42 | 99.5 | 1.5  | 85.6 | 1.2 | 3.3 | 5.5  | 1.1 |
| 6  | 150 | 16 | 0.40 | 99.6 | 0.4  | 88.7 | 1.2 | 3.2 | 4.0  | 1.2 |
| 7  | 150 | 8  | 0.40 | 99.5 | 5.7  | 80.7 | 1.0 | 5.2 | 3.7  | 2.2 |
| 8  | 140 | 16 | 0.41 | 99.5 | 1.8  | 86.3 | 1.0 | 3.4 | 4.3  | 2.0 |
| 9  | 145 | 16 | 0.40 | 99.5 | 1.5  | 86.1 | 0.9 | 3.4 | 4.9  | 2.0 |
| 10 | 150 | 16 | 0.40 | 99.5 | 2.5  | 86.1 | 1.0 | 3.3 | 4.4  | 1.6 |
| 11 | 150 | 16 | 0.40 | 99.5 | 0.6  | 88.5 | 1.1 | 2.3 | 4.7  | 1.4 |

Example 3

A second reactor for hydrogenation was added to the system on the exit side of the HDH reactor. This reactor consisted of an Inconel™ 600 tube ⅜" (9.5 mm) od.×0.035" (0.9 mm) wall, 30" (762 mm) longs packed with 27.8 grams (35.9 mL) of (0.5 weight % palladium on acid washed 12–30 mesh carbon (1.68–0.59 mm). The catalyst was treated with 120 sccm (2.0×10$^{-6}$ m$^3$/s) of hydrogen at 150° C. for one hour prior to the run. The HDH reactor was the same as that used in Example 1. It was packed with 21.7 g of the HDH catalyst and treated with 120 sccm (2.0×10$^{-6}$ m$^3$/s) of hydrogen at 350° C. for one hour prior to the run. The entire effluent of the HDH reactor (including HCl and HF) was passed into the second (hydrogenation) reactor. The contact time in the HDH reactor was 0.14 minutes for run 1, 0.13 minutes for runs 2, 3 and 6, and 0.07 minutes for runs 4 and 5. The temperature for the HDH reaction was 350° C. for run 1, 355° C. for runs 2, 3, 4 and 6 and 360° C. for run 5. The contact time (CT) shown in the table is for the Pd/C catalyst. The temperature of the hydrogenolysis reaction was 150° C. for all runs. The pressure of both reactors was 40 psig (377 kPa). Results of these reactions are shown in the Table 3.

TABLE 3

| Run No. | Molar Ratio H$_2$:216aa | CT Min. | % Conv. 216aa | % Sel. to | | | | | | |
|---|---|---|---|---|---|---|---|---|---|---|
| | | | | 1225zc | 236fa | 245fa | 254fb | 226da | 235da | 225da |
| 1  | 16 | 0.25 | 100 | 0.6 | 6.1  | 87.9 | 1.6 | 1.3 | 0.8 | 0.2  |
| 2  | 16 | 0.25 | 100 | 0.5 | 5.9  | 88.1 | 1.6 | 1.5 | 1.0 | <0.1 |
| 3  | 16 | 0.25 | 100 | 0.4 | 6.5  | 86.0 | 1.7 | 2.1 | 1.8 | <0.1 |
| 4  | 16 | 0.13 | 100 | 0.5 | 19.7 | 68.9 | 1.4 | 6.4 | 1.6 | <0.1 |
| 5  | 16 | 0.13 | 100 | 0.4 | 18.0 | 69.1 | 1.4 | 7.5 | 2.0 | <0.1 |
| 11 | 16 | 0.25 | 100 | 0.3 | 10.2 | 77.7 | 1.7 | 5.4 | 3.2 | <0.1 |

Example 4

The reactor used for hydrodehalogenation (HDH) in Example 1 was charged with catalyst (24.1 g, 18.0 mL) ⅛"×⅛" (3.2 mm×3.2 mm) pellets prepared substantially in accordance with the Catalyst Preparation above. The HDH catalyst unlike that of Example 1 was not used previously, i.e., it was a fresh catalyst. Before starting the runs shown in Example 1, the HDH catalyst was treated with 110 sccm (1.8×10$^{-6}$ m$^3$/s) H$_2$ at 350° C. and 40 psig (380 kPa) for one hour.

CF$_3$CCl$_2$CF$_3$ and H$_2$ were contacted with the catalyst at 350° C. or 360° C. and with a molar ratio of H$_2$:CF$_3$CCl$_2$CF$_3$ as shown in the table. All runs were conducted at a pressure of 40 psig (380 kPa). Results of the HDH reaction are shown in Table 4.

TABLE 4

| Run No. | HDH[1] T (° C.) | Molar Ratio H$_2$:216aa | CT Min. | % Conv. 216aa | % Sel. to | | |
|---|---|---|---|---|---|---|---|
| | | | | | 1225zc | 1215xc | Other[2] |
| 1 | 350 | 16 | 0.27 | 100 | 9.1 | 87.4 | 3.6 |
| 2 | 350 | 16 | 0.27 | 100 | 10.2 | 86.2 | 3.7 |
| 3 | 350 | 8 | 0.27 | 100 | 12.0 | 84.0 | 4.0 |
| 4 | 350 | 16 | 0.27 | 100 | 10.9 | 84.8 | 4.2 |

[1]HDH is the hydrodehalogenation catalyst
[2]Other includes 236fa, 245fa and 226da Example 5

The reactor and catalyst used for hydrodehalogenation (HDH) in Example 3 was used. The HDH catalyst was treated prior to use with hydrogen at 300° C. for one hour; 67% air/33% N$_2$ at 300° C. for 1 hour; 50% air/50% N$_2$ at 400° C. for 1 hour; air at 450° C. for 2 hours; air at 500° C. for 5 hours; air at 550° C. for 5 hours; followed by purging with N$_2$ at 350° C. for 3 hours; N$_2$/H$_2$ (1:1) at 350° C. for one hour; and finally reduced with H$_2$ at 350° C. for one hour.

CF$_3$CCl$_2$CF$_3$ and H$_2$ were contacted with the catalyst at 350° C. and with a molar ratio of H$_2$:CF$_3$CCl$_2$CF$_3$ as shown in the Table 4. The HDH reaction was done at a pressure of 40 psig (380 kPa) and a contact time of 0.27 minutes. The entire effluent (including HCl and HF) was then passed into a second (hydrogenation) reactor which was the same as that used in Example 3 and contained the same catalyst. The hydrogenation catalyst was purged with hydrogen at 380 kPa and 150° C., the same temperature and pressure as the hydrogenation reaction,. for 8 hours prior to use. The contact time of the hydrogenation reaction was 0.51 minutes. The results of the combined reactions arc shown in Table 5.

TABLE 5

| Run No. | Molar Ratio H$_2$:216aa | % Conv. 216aa | % Sel. to | | | | | |
|---|---|---|---|---|---|---|---|---|
| | | | 1225zc | 245fa | 254fb | 226da | 235da | Other[1] |
| 1 | 16 | 100 | 0.0 | 89.0 | 2.7 | 0.1 | 4.6 | 3.6 |
| 2 | 8 | 100 | 3.8 | 80.6 | 2.1 | 1.0 | 9.2 | 3.3 |
| 3 | 8 | 100 | 4.8 | 81.3 | 2.0 | 1.2 | 7.6 | 2.9 |

[1]Other includes 236fa and 1225xc

Example 6

The reactor and catalyst used for hydrodehalogenation (HDH) in Example 4 was used. The HDH catalyst was treated prior to use in the same way as the catalysts used in Example 4.

CF$_3$CCl$_2$CF$_3$ and H$_2$ were contacted with the catalyst at 350° C. and with a molar ratio of H$_2$:CF$_3$CCl$_2$CF$_3$ as shown in the Table 4. The HDH reaction was done at a pressure of 40 psig (380 kPa) and a contact time of 0.27 minutes except for run 3 which was done at 0.13 minutes. The entire effluent (including HCl and HF) was then passed into a second (hydrogenation) reactor which was the same as that used in Example 3 and contained the same catalyst. The hydrogenation catalyst was purged with hydrogen at 380 kPa and 150° C., the same temperature and pressure as the hydrogenation reaction, for 8 hours prior to use. The contact time of the hydrogenation reaction was 0.51 minutes except for run 3 which was 0.25 minutes. The results of the combined reactions are shown in Table 6.

TABLE 6

| Run No. | Molar Ratio H$_2$:216aa | % Conv. 216aa | % Sel. to | | | | | |
|---|---|---|---|---|---|---|---|---|
| | | | 1225zc | 245fa | 254fb | 226da | 235da | Other[1] |
| 1 | 16 | 100 | 0.4 | 81.0 | 3.7 | 1.0 | 9.4 | 0.2 |
| 2 | 16 | 100 | 1.1 | 73.9 | 3.7 | 1.0 | 14.0 | 0.2 |
| 3 | 16 | 100 | 7.4 | 74.1 | 2.5 | 1.0 | 11.6 | 0.2 |
| 4 | 8 | 100 | 11.5 | 66.4 | 1.8 | 1.8 | 10.1 | 0.2 |

[1]Other includes 236fa and 1225xc

Example 7

$CF_3CH=CF_2 + HF \rightarrow CF_3CH_2CF_3$ (Liquid Phase)

A Hastelloy™ nickel alloy (160 mL) autoclave equipped with a magnetically driven stirrer, pressure transducer, thermocouple well, and vapor inlet valve was evacuated, cooled in liquid nitrogen, and charged with anhydrous HF (50 g, 2.5 moles). 1,1.3,3,3-Pentafluoro-1-propene (20.2 g, 0.15 mole) was added to the autoclave at a temperature of about −31° C. from a small cylinder. The autoclave was then warmed to ambient temperature. The contents of the autoclave were stirred at about 500 rpm and the autoclave was heated to 70° C. over the course of about 8 minutes. The pressure rose to 106 psig (832 kPa) and then leveled out at 99 psig (784 kPa). After 2 hours at 71 ° C. and 99 psig (784 kPa), a sample of the vapor phase of the autoclave was analyzed by GC-MS (see Table 7).

TABLE 7

| Component | GC Area % |
|---|---|
| C$_3$F$_6$ | 0.3 |
| 1225zc | 84.9 |
| 236fa | 14.3 |

Example 8

$CF_3CH=CF_2 + HF \rightarrow CF_3CH_2CF_3$ (Vapor Phase)

A 15 mL tubular reactor was packed with 13.7 g of a catalyst comprising a 0.02:0.98:1.0 ratio of CoF$_2$, ZnF$_2$, and AlF$_3$, respectively. The catalyst was activated by heating to 250° C. over the course of 1 hour while passing 50 sccm (8.3×10$^{-7}$ m$^3$/s) nitrogen through the reactor. The nitrogen flow was then reduced to 20 sccm (3.3×10$^{-7}$ m$^3$/s) and HF was admitted at 50 sccm (8.3×10$^{-7}$ m$^3$/s) at 250° C. for 1 hour.

A 4:1 molar mixture of HF and 1,1,3,3,3-pentafluoro-1-propene was fed to the reactor with a catalyst contact time of 15 seconds at 300° C. A comparison of the reactor feed gas and effluent under these conditions is given in Table 8.

TABLE 8

| Temp. ° C. | 143a | HFP | 1225zc | 236fa | 125 |
|---|---|---|---|---|---|
| Feed | 0.0 | 0.2 | 98.4 | 0.6 | 0.0 |
| 350 | 0.2 | 0.1 | 1.4 | 97.8 | 0.1 |
| 300 | 0.1 | 0.1 | 0.4 | 98.9 | 0.0 |

Other products observed by GC include CH$_3$Cl, CH$_3$F, CHF$_2$CClF$_2$, and CHClFCF$_3$ which appear to be contaminants in the 1225zc.

What is claimed is:

1. An azeotropic composition comprising from about 70.1 to 58.7 mole percent of CF$_3$CHFCF$_3$, and HF, wherein said HF is present in an amount effective to form an azeotropic composition with said CF$_3$CHFCF$_3$.

2. The azeotropic composition of claim 1 which consists essentially of from about 29.9 to about 41.3 mole percent HF and from about 70.1 to 58.7 mole percent CF$_3$CHFCF$_3$.

3. A process for producing compositions comprising (c1) a compound selected from the group consisting of CF$_3$CHFCF$_3$, CF$_3$CH$_2$CF$_3$ and CHF$_2$CH$_2$CF$_3$ and (c2) at least one saturated compound selected from halogenated hydrocarbons and ethers having the formula $$C_nH_{2n+2-a-b}Cl_aF_bO_c$$

wherein n is an integer from 1 to 4, a is an integer from 0 to 2n+1, b is an integer from 1 to 2n+2−a, and c is 0 or 1, provided that when c is 1 then n is an integer from 2 to 4, and provided that component (c2) does not include the selected component (c1) compound wherein the molar ratio of component (c2) to component (c1) is between about 1:99 and a molar ratio of HF to component (c1) in an azeotrope or azeotrope-like composition of component (c1) with HF, comprising:

(A) combining (i) said azeotrope or azeotrope-like composition with (ii) at least one fluorination precursor compound wherein the precursor component (ii) is the fluorination precursor to component (c2); and (B) reacting a sufficient amount of the HF from the azeotrope or azeotrope-like composition (i) with precursor component (ii) to provide a composition containing components (c1) and (c2) in said ratio.

4. The process of claim 3 wherein component (c1) is CF$_3$CHFCF$_3$; wherein the molar ratio of component (c2) to CF$_3$CHFCF$_3$ is between about 1:99 and about 41.3:58.7; and wherein in (A) an azeotrope or azeotrope-like composition consisting essentially of CF$_3$CHFCF$_3$ and HF wherein the ratio of HF to CF$_3$CHFCF$_3$ is at least about the desired ratio is combined with (ii).

5. The process of claim 3 wherein component (c1) is CF$_3$CH$_2$CF$_3$; wherein the molar ratio of component (c2) to CF$_3$CH$_2$CF$_3$ is between about 1:99 and about 59:41: and wherein in (A) an azeotrope or azeotrope-like composition consisting essentially of CF$_3$CH$_2$CF$_3$ and HF wherein the ratio of HF to CF$_3$CH$_2$CF$_3$ is at least about the desired ratio is combined with (ii).

6. The process of claim 3 wherein component (c1) is CHF$_2$CH$_2$CF$_3$; wherein the molar ratio of component (c2) to CHF$_2$CH$_2$CF$_3$ is between about 1:99 and about 84:16; and wherein in (A) an azeotrope or azeotrope-like composition consisting essentially of CHF$_2$CH$_2$CF$_3$ and HF wherein the ratio of HF to CHF$_2$CH$_2$CF$_3$ is at least about the desired ratio is combined with (ii).

7. An azeotropic composition comprising CF$_3$CHFCF$_3$ and HF, wherein said HF is an amount of from about 29.9 to 41.3 mole percent.

8. A composition comprising:

(c1) a compound selected from the group consisting of CF$_3$CHFCF$_3$, CF$_3$CH$_2$CF$_3$ and CHF$_2$CH$_2$CF$_3$; and (c2) at least two saturated compounds selected from halogenated hydrocarbons and ethers having the formula:

$$C_nH_{2n+2-a-b}Cl_aF_bO_c \qquad 5$$

wherein n is an integer from 1 to 4, a is an integer from 0 to 2n+1, b is all integer from 1 to 2n+2−a, and c is 0 or 1, provided that when c is 1 then n is an integer from 2 to 4, and provided that component (c2) does not include the selected component (c1) compound and provided that c is 1 for at least one of the component (c2) compounds, wherein the molar ratio of component (c2) to component (c1) is between 1:99 and 41.3:58.7 when component (c1) is $CF_3CHFCF_3$, between 1:99 and 59:41 when component (c1) is $CF_3CH_2CF_3$, and between 1:99 and 84:16 when component (c1) is $CHF_2CH_2CF_3$.

* * * * *

UNITED STATES PATENT AND TRADEMARK OFFICE
CERTIFICATE OF CORRECTION

PATENT NO. : 6,376,727 B1  Page 1 of 1
DATED : April 23, 2002
INVENTOR(S) : V.N.M. Rao et al.

It is certified that error appears in the above-identified patent and that said Letters Patent is hereby corrected as shown below:

Column 1,
Line 6, please insert:
-- This application represents a national filing under 35 USC 371 of International Application No. PCT/US98/03132 filed February 18, 1998, and claims priority of U.S. Provisional Application No. 60/056,795 filed August 25, 1997 and U.S. Provisional Application No. 60/049,723 filed June 16, 1997. --

Column 9,
Line 51, please delete "$CH_2CF_2$" and insert -- $CH_2F_2$ --.

Signed and Sealed this

Tenth Day of February, 2004

JON W. DUDAS
*Acting Director of the United States Patent and Trademark Office*